United States Patent
Hilgeroth

(10) Patent No.: US 9,901,570 B2
(45) Date of Patent: Feb. 27, 2018

(54) BREAST CANCER CELL GROWTH-INHIBITING ENZYME INHIBITORS, METHOD FOR THE PRODUCTION THEREOF, AND USE THEREOF

(71) Applicant: Martin-Luther-Universitaet Halle-Wittenberg, Halle (Saale) (DE)

(72) Inventor: Andreas Hilgeroth, Halle (DE)

(73) Assignee: Martin-Luther-Universitaet-Halle-Wittenberg, Halle (Saale) (DE)

(*) Notice: Subject to any disclaimer, the term of this patent is extended or adjusted under 35 U.S.C. 154(b) by 0 days.

(21) Appl. No.: 14/900,366

(22) PCT Filed: Aug. 21, 2014

(86) PCT No.: PCT/IB2014/002141
§ 371 (c)(1),
(2) Date: Apr. 25, 2016

(87) PCT Pub. No.: WO2014/207573
PCT Pub. Date: Dec. 31, 2014

(65) Prior Publication Data
US 2016/0235723 A1    Aug. 18, 2016

(30) Foreign Application Priority Data
Jun. 26, 2013  (DE) .................. 10 2013 010 603

(51) Int. Cl.
C07D 471/04    (2006.01)
A61K 31/4375   (2006.01)
A61K 31/437    (2006.01)

(52) U.S. Cl.
CPC ........ *A61K 31/437* (2013.01); *A61K 31/4375* (2013.01); *C07D 471/04* (2013.01)

(58) Field of Classification Search
None
See application file for complete search history.

(56) References Cited

U.S. PATENT DOCUMENTS

2007/0004684 A1 * 1/2007 Sennhenn ............ C07D 471/04
                                                         514/150

* cited by examiner

*Primary Examiner* — Niloofar Rahmani
(74) *Attorney, Agent, or Firm* — Norris McLaughlin & Marcus, P.A.

(57) ABSTRACT

Novel enzyme inhibitors for treatment of breast cancer combine the inhibition of enzymes that combat aggressive breast cell growth both synergistically and additively. Pyrido-annulated indoles developed act in a selectively inhibiting manner on the enzymes HER2 and/or Brk in the nanomolar to picomolar concentration range in screening more than 200 kinases of the human kinome. The enzyme inhibitors inhibit the growth of breast cancer cells in the nanomolar concentration range without exhibiting critical toxic effects. The derivatization at the 6-position of the 4-chloro-α-carboline is achieved without by-products and, similarly to the derivatization at the 4-position with the aniline derivatives, takes place at high purity with quantitative yields.

4 Claims, No Drawings

BREAST CANCER CELL GROWTH-INHIBITING ENZYME INHIBITORS, METHOD FOR THE PRODUCTION THEREOF, AND USE THEREOF

BACKGROUND OF THE INVENTION

According to epidemiological data, breast cancer is the most frequent form of cancer in women [1]. Particularly aggressive breast cancers are characterized by invasive and metastatic behavior [2]. The treatment of such aggressive breast cancers is extremely problematic and very costly due to the use of specific antibodies, which are employed only after multiple positive histochemical tests [3].

The cause for the aggressive qualities of the tumors lies in the overexpression of cell membrane-bound receptors [4]. The action of these receptors is overexpression with uncontrolled stimulation of cell proliferation and inhibition of controlled cell death, or apoptosis [5, 6].

The uncontrolled cell proliferation results in rapid tumor growth. It is particularly critical when apoptosis of the aggressive tumor cells is suppressed at the same time [2].

The survival prognosis of such breast cancer diseases is extremely low [3]. Treatment with the antibody trastuzumab is not only very costly, but also fails when the HER2 receptor, to which trastuzumab binds, has been degenerated as a result of mutations. The receptor is then constitutively active and cannot be inhibited by the antibody [3, 4].

According to recent findings, a second factor plays another important role in aggressive breast cancers. This is the enzyme Brk, which is overexpressed in the aggressive tumor cells like HER2 [2, 4, 7]. The activity of HER2 is amplified further by Brk [2, 7]. Brk thus not only amplifies the uncontrolled growth of the tumor cells, but also inhibits the apoptosis of the same [2,8-11]. The aggressiveness of the tumor cells is further increased by Brk in that the formation of metastases is amplified [2]. This is a consequence of the fact that the tumor cells do not die off after detaching from the tumor cell group and a separate tumor cell group is formed [2].

The only possible treatment of such aggressive breast cancers is with inhibitors. A previously used HER2 inhibitor called lapatinib, however, shows effects only in a limited number of cases [4]. Failure of the inhibitor therapies conducted until now has been blamed on tumor cell resistances, which are a result of mutations of HER2, among other things. An inhibitor against Brk and HER2 is not known to date.

SUMMARY OF THE INVENTION

It is the object of the invention to develop novel enzyme inhibitors by combining the inhibition of enzymes that combat aggressive breast cell growth both synergistically and additively. An existing resistance to inhibitors is overcome by the new inhibitors, and an emerging resistance over the course of a therapy can be suppressed by the mechanism of action.

The pyrido-annulated indoles developed according to the invention act in a selectively inhibiting manner on the enzymes HER2 and/or Brk in the nanomolar to picomolar concentration range in screening more than 200 kinases of the human kinome. Dual inhibitions allow resistant tumors to be treated, which previously has not been possible. Moreover, development of resistance is suppressed.

The breast cancer cell growth-inhibiting enzyme inhibitors of the invention are functional pyrido-annulated indoles and pyrido pyrroles of general formula

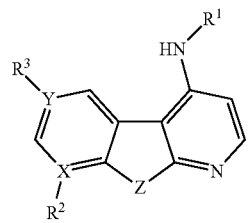

in which each of X and Y=C, or X=C and Y=N or X=N and Y=C, and in which Z=NH,
and wherein
R1=Ph-3- or 4-CONH—R3 or 4-halogen or 4-OBn, —CN, —Cl, —Br, —F (-halogen), —OH, —CH3, —OCH3, —OC2H5, —OBn (-Oalkyl), —CF3, —NO2, —NH2, —NHCO alkyl, —SCH3; Ph-3- and 4-CONH—R3 or 4-halogen or 4-OBn, —CN, —Cl, —Br, —F (-halogen), —OH, —CH3, —OCH3, —OC2H5 (-Oalkyl), —CF3, —NO2, —NH2, —NHCO alkyl, —SCH3
R2=Br (-halogen), NO2, NH2
R3=H, Br (halogen), heteroaryl, NH2, NHR4, NO2, CN, COOR4, NHSO2R4, NHCOR4, NHCOOR4, NHCONHR4, COalkyl, SO2NHR4, NHCONR5R6, SO2NR5R6
R4=alkyl, aminoalkyl, piperazinoalkyl, N-morpholinoalkyl, hydroxyalkyl
R5, R6=alkyl; —CH2-CH2-T-CH2-CH2-, T=O, NH, NR4.

The enzyme inhibitors developed according to the invention inhibit the growth of breast cancer cells in the nanomolar concentration range without exhibiting critical toxic effects. In this regard, they differ from other tumor therapeutics, which due to cell-toxic effects during treatment cause a wide range of side effects, and are consequently not very compatible.

To date, pyrido-fused indoles with substituents in the 4 and 6 positions [13], with a 2,3-substituted aniline in the 4-position and an aryl radical in the 6-position inhibit a single protein kinase (ALK1). In contrast, pyrido-fused indoles described in this specification have no aryl residues in the 6-position and are unsubstituted in the 2-position of the 4-aniline residue. The inventors of the present application observe enzyme inhibitory activity only in the case of substitution patterns described in this application. On the other hand, 6-aryl- and 4- (2-anilino) substituted derivatives are not effective because of steric problems in the enzyme interaction. It has been surprisingly found that pyrido-fused indoles with only the 4-substitution (can be arylamine radicals) show antiviral activity [14,15]. The pyrido-fused indoles according to the invention described herein are enzyme-inhibiting with 3,4-disubstituted residues and show no antiviral activity. The enzyme-inhibiting effect is due to the 3,4-disubstitution of the 4-aniline radical and the given 6 and 8 substitution of the basic body.

The derivatization at the 6-position of the 4-α-alpha-carboline is achieved without byproducts and, similarly to the derivatization at the 4-position with the aniline derivatives, takes place at high purity with quantitative yields.

DETAILED DESCRIPTION OF THE INVENTION

Exemplary Embodiment

An equivalent 4-chlor-α-carboline was loaded in a two-necked flask comprising a reflux condenser and gas discharge and cooled with an ice bath. Thereafter, 1.5 mL chlorosulfonic acid was slowly added dropwise while stirring. After addition, the ice bath was removed and the mixture was stirred at room temperature until starting material was no long detectable by way of TLC. The excess chlorosulfonic acid was then hydrolyzed while cooling. The precipitated solid matter was filtered off, washed with cold water, and dried. The solid was then resuspended in 25 mL THF and mixed with 20 equivalents of the amine in question while stirring. The mixture was stirred at room temperature until starting material was no longer detectable by way of TLC; then the solvent was removed under reduced pressure and the residue was mixed with water. The precipitated residue was filtered off and dried.

The derivatization with anilines took place with an equivalent of the 6 derivative of the 4-chlor-α-carboline in anhydrous n-methylpyrrolidone while degassing, and subsequent boiling under reflux until starting material was no longer detectable by way of TLC. After cooling, the mixture was separated by way of column chromatography without further processing. The combined product fractions were poured into ice water, and the precipitated product was then filtered off and dried.

The alternative basic bodies with X=C and Y=N and X=N and Y=C are prepared from one equivalent of 2,3-dichloropyridine and 1.2 equivalents of 4- or 2-aminopyridine in a palladium acetate-catalyzed (2 mol %) reaction under basic conditions using potassium carbonate in toluene under reflux overnight. In the resulting 3-chloro- (4- and 2-pyridylamiono) pyridines, the ring closure is again carried out in a palladium-catalyzed reaction using Pd2 (dba) 3 (10 mol %) and tri-t-butylphosphine (40 mol %) under potassium phosphate addition in dioxane at 120° C. The 4-chloro substituent is introduced with one equivalent of the basic body by means of 1.6 equivalents of hydrogen peroxide solution (35%) in glacial acetic acid under boiling at reflux and then 4-chlorination in DMF by means of 2.4 equivalents of phosphorus oxychloride at room temperature.

The 8-derivatization of the 6-substituted compounds was carried out with an excess of red fuming nitrating acid or bromine at room temperature.

The enzyme inhibitors are obtained regioselectively since the substitutions are selectively controlled by the electron-shifting NH function of the parent bodies under gentle conditions of room temperature. This ensures an almost by-product-free reaction and enables the purification of pure products with a nearly quantitative yield by means of column chromatographic separation.

Inhibition of the enzymes Brk and HER2 was carried out using ATP enriched with radioactively labeled ATP and the substrate poly(gly,tyr) 4:1 using different concentrations of inhibitors in HEPES buffer solution. The percentage inhibition of the enzymes is determined by way of measuring substrate phosphorylation by way of scintillation measurement. The percentage inhibition was used to calculate the IC50 of the enzyme inhibition. For a meta-chlorine substituted aniline derivative, it was 5 nM for the inhibition of Brk and 66 nM for the inhibition of HER2.

The breast cancer cell growth-inhibiting action was determined in a sulforhodamine B assay. For this purpose, the different breast cancer cell lines were cultivated in RPMI 1640-medium, which contained 5% fetal calf serum and 2 nM L-glutamine. After 24 hours of cultivation at 37° C. and 100% humidity under a $CO_2$ atmosphere (5%), incubation was carried out with different inhibitor concentrations in microtiter plates. Subsequently, the adhering cells were fixed with 50% trichloroacetic acid. After renewed incubation, the supernatant was discarded, and the cells were washed with sulforhodamine B solution mixed with acetic acid. After renewed incubation, they were washed, and the sulforhodamine B dye dissolved under the addition of Tris buffer was spectroscopically measured. The growth inhibition was ascertained via the different amounts of dye in the comparison of untreated and inhibitor-treated cell lines. For a meta-methoxy substituted aniline derivative, 50% growth inhibition was achieved in all breast cancer cell lines at nanomolar inhibitor concentrations compared to HER2. A para-methoxy-substituted aniline derivative showed a 26% inhibition of growth at nanomolar inhibitory concentrations compared to Brk. A dual nanomolar inhibitor of HER2 and Brk resulted in a 65% inhibition of growth with a meta-chloroaniline function.

LITERATURE

[1] http://www.krebsgesellschaft.de/krebshäufigkeit.
[2] Harvey, A. J. et al. Am. J. Pathol. (2009), published online Aug. 6, 2009, DOI:10.2353/ajpath.2009.08.811.
[3] Untch, M. et al. Dtsch Arztebl. (2006), 103 (50), A-3406/B-2961/C-2841.
[4] Cold Spring Harbor Laboratory (2008, Aug. 26), Science Daily, retrieved Jun. 17, 2001, from http://www.sciencedaily.com/releases/2008/08/080825103533.htm
[5] Olayioye, M. A. Breast Cancer Res. (2001), 3, 385.
[6] Hanahan, D, Weinberg, R. A. Cell (2000), 100, 57.
[7] Born, M. et al. J. Pathol. (2005), 205, 592.
[8] Harvey, A. J. Crompton, M. R. Oncogene (2003), 22, 5006.
[9] Frisch, S. M, Francis H. J. Cell. Biol. (1994), 124, 619.
[10] Kamalati, T. et al. J. Biol. Chem. (1996), 271, 30956.
[11] Xiang, B. et al. Proc. Natl. Acad. Sciences (2008), DOI:10.1073/pnas.0805009105.
[12] Gambacorti-Passerini, C. et al. EP 2 662 372 A1;
[13] Elks, J. et al. BP 1268773;
[14] Elks, J. et al. DE 1913124.

The invention claimed is:

1. A compound consisting of functional pyrido-fused indoles and pyridopyrole of the general formula

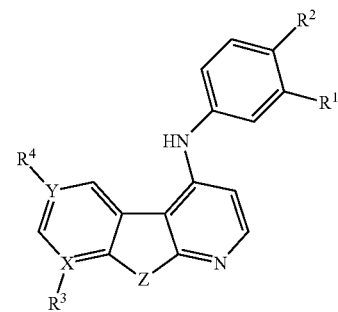

wherein
each of X and Y=C, or X=C and Y=N, or X=N and Y=C, and
Z=NH,
and
$R_1$ is CN, Cl, Br, F, OH, CH3, OCH3, OC2H5, OBn, CF3, NO2, NH2, NHCO-alkyl, or SCH3, and
R2 is CONHR5, halogen or Obn,
or
R1=H, and
R2=CONHR5, halogen or Obn, or
R1 is CN, Cl, Br, F, OH, CH3, OCH3, OC2H5, OBn, CF3, NO2, NH2, NHCO-alkyl or SCH3, and
R2=H,
and
R3=Br, NO2 or NH2, for X=C, Y=C or X=C, Y=C or N, and
R4 is H, Br, heteroaryl, NH2, NHR5, NO2, CN, COOR5, NHSO2R5, NHCOR5, NHCOOR, NHCONHR5, COalkyl, SO2NHR5, NHCONR6R7 or SO2NR6R7, for X=C, Y=C or X=N, Y=C, and
R5=alkyl, aminoalkyl, piperazinoalkyl, N-morpholino-alkyl, or hydroxyalkyl, and
each of R6 and R7=alkyl, —CH2-CH2-O—CH2-CH2, —CH2-CH2-NH—CH2-CH2-, or —CH2-CH2-NR5-CH2-CH2-,
wherein the compound is a breast cancer cell growth-inhibiting enzyme inhibitor.

2. A method for preparing the compound according to claim 1 regioselectively, wherein in said compound, X=C, Y=C and Z=NH, said method comprising,
1) reacting 4-chloro-α-carboline with chlorosulfonic acid and collecting precipitate formed,
2) resuspending the precipitate formed in step 1) and mixing it with an amine at room temperature,
3) filtering and drying precipitated residue formed at the end of step 2),
4) mixing the filtered and dried residue formed at the end of step 3) with anhydrous n-methylpyrrolidone,
5) separating the mixture formed at the end of the step 4) and collecting solid precipitate separated from the mixture, and
6) filtering and drying the solid precipitate collected at the end of step 5).

3. A method for treating aggressive breast cancer in a patient afflicted with aggressive breast cancer, comprising:
administering to the patient a therapeutically effective amount of the compound according to claim 1 as inhibitors of Brk and HER2,
wherein the therapeutically effective amount of the compound is synergistically effective in treating the aggressive breast cancer.

4. A method for treating inhibitor-resistant breast cancer in a patient afflicted with inhibitor-resistant breast cancer, comprising:
administering to the patient a therapeutically effective amount of the compound according to claim 1 as inhibitors Brk and HER2,
wherein the compound is a selectively tumor-apoptotic breast cancer cell growth-inhibiting enzyme inhibitor.

* * * * *